United States Patent
Petyt et al.

(10) Patent No.: US 9,638,698 B2
(45) Date of Patent: *May 2, 2017

(54) EMBOSSED CELL ANALYTE SENSOR AND METHODS OF MANUFACTURE

(71) Applicant: Abbott Diabetes Care Inc., Alameda, CA (US)

(72) Inventors: Adrian Petyt, Chipping Norton (GB); Simon A. Hector, Swindon (GB)

(73) Assignee: Abbott Diabetes Care Inc., Alameda, CA (US)

( * ) Notice: Subject to any disclaimer, the term of this patent is extended or adjusted under 35 U.S.C. 154(b) by 666 days.

This patent is subject to a terminal disclaimer.

(21) Appl. No.: 14/155,129

(22) Filed: Jan. 14, 2014

(65) Prior Publication Data

US 2014/0127821 A1    May 8, 2014

Related U.S. Application Data

(60) Continuation of application No. 13/489,161, filed on Jun. 5, 2012, now Pat. No. 8,632,965, which is a continuation of application No. 12/815,170, filed on Jun. 14, 2010, now Pat. No. 8,211,632, which is a continuation of application No. 11/935,176, filed on Nov. 5, 2007, now Pat. No. 7,771,926, which is a division of application No. 11/552,234, filed on Oct. 24, 2006, now Pat. No. 7,312,042.

(51) Int. Cl.
| | |
|---|---|
| *C12Q 1/00* | (2006.01) |
| *G01N 33/66* | (2006.01) |
| *A61B 5/145* | (2006.01) |
| *G01N 27/327* | (2006.01) |

(52) U.S. Cl.
CPC ............. *G01N 33/66* (2013.01); *A61B 5/145* (2013.01); *C12Q 1/006* (2013.01); *G01N 27/3272* (2013.01); *Y02P 20/582* (2015.11); *Y10T 29/49004* (2015.01); *Y10T 29/49764* (2015.01); *Y10T 29/49826* (2015.01); *Y10T 436/144444* (2015.01)

(58) Field of Classification Search
None
See application file for complete search history.

(56) References Cited

U.S. PATENT DOCUMENTS

| | | | |
|---|---|---|---|
| 4,957,615 A | | 9/1990 | Ushizawa |
| 4,988,630 A | * | 1/1991 | Chen ................... G01N 21/253 422/73 |
| 5,885,429 A | | 3/1999 | Friese et al. |
| 6,103,033 A | | 8/2000 | Say et al. |
| 6,590,207 B2 | | 7/2003 | Berger et al. |
| 6,766,817 B2 | | 7/2004 | da Silva |
| 6,918,404 B2 | | 7/2005 | da Silva |
| 6,994,827 B2 | | 2/2006 | Safir et al. |
| 7,058,437 B2 | | 6/2006 | Buse et al. |
| 7,066,586 B2 | | 6/2006 | da Silva |
| 7,312,042 B1 | * | 12/2007 | Petyt .................. G01N 27/3272 435/7.1 |
| 7,771,926 B2 | * | 8/2010 | Petyt .................. G01N 27/3272 435/4 |
| 8,211,632 B2 | * | 7/2012 | Petyt .................. G01N 27/3272 435/4 |
| 8,632,965 B2 | * | 1/2014 | Petyt .................. G01N 27/3272 435/4 |
| 2004/0067166 A1 | | 4/2004 | Karinka et al. |
| 2004/0118704 A1 | | 6/2004 | Wang |
| 2005/0019212 A1 | | 1/2005 | Bhullar et al. |
| 2006/0144704 A1 | | 7/2006 | Ghesquiere |
| 2007/0259431 A1 | * | 11/2007 | Charlton ............... B01L 3/5027 436/2 |
| 2011/0000283 A1 | * | 1/2011 | van 't Oever ........ B81C 99/004 73/40 |

FOREIGN PATENT DOCUMENTS

| | | |
|---|---|---|
| EP | 1482299 | 12/2004 |
| JP | 9201337 | 8/1997 |
| JP | 2000509507 | 7/2000 |
| JP | 2002541453 | 12/2002 |
| RU | 2258922 | 8/2005 |
| WO | 2004/083843 | 9/2004 |
| WO | 2004/113900 | 12/2004 |
| WO | 2005/008231 | 1/2005 |

* cited by examiner

*Primary Examiner* — Ann Lam
(74) *Attorney, Agent, or Firm* — Edward J. Baba; Bozicevic, Field & Francis LLP

(57) ABSTRACT

An analyte measurement system is provided having sensors with embossed test chamber channels. In one embodiment, the sensors are elongate test strips for in vitro testing, each test strip having a substrate, at least one electrode, an embossed channel in the electrode, and lidding tape covering at least a portion of the embossed channel. Methods of manufacture are also disclosed for filling the sensor channels with reagent, and for trimming the ends of the sensors to eliminate the need for a calibration code during use of the sensors with a meter.

15 Claims, 5 Drawing Sheets

EMBOSSED CELL ANALYTE SENSOR AND METHODS OF MANUFACTURE

This application is a divisional application of U.S. application Ser. No. 11/552,234 filed Oct. 24, 2006, the disclosure of which is incorporated herein by reference.

FIELD OF THE INVENTION

The present invention relates to medical devices for monitoring analyte in a living body, such as monitoring glucose levels in people with diabetes. More particularly, the invention relates to an analyte sensor having an embossed sample chamber.

BACKGROUND OF THE INVENTION

People with diabetes typically measure their blood glucose level by lancing a finger tip or other body location to draw blood, applying the blood to a disposable test strip in a hand-held meter and allowing the meter and strip to perform an electrochemical test of the blood to determine the current glucose concentration. Such in vitro tests are typically conducted at least several times per day. Detailed descriptions of such glucose monitoring systems and their use are provided in U.S. Pat. No. 7,058,437, issued to TheraSense, Inc. on Jun. 6, 2006, which is incorporated by reference herein in its entirety.

In addition to the examples provided in U.S. Pat. No. 7,058,437, there have been numerous other approaches to test strip sensor construction in the field of in vitro blood glucose monitoring. Two common methods are described below.

In the first common method of test strip construction, a mesh, insulation and lidding tape arrangement is used. In this method, a base electrode is first formed on a substrate. A surfactant-coated mesh is then adhered to the base electrode by an overprinted layer of insulation ink. The ink is applied in a printed pattern. The open (non-printed) area of the pattern forms the sample cell and defines the working area on the base electrode. A lidding tape is then adhered to the upper surface of the insulation printing leaving sufficient openings for the air to escape as the strip fills with blood during use.

A disadvantage of this method is that print registration accuracy and ink rheology limits the smallest size of cell that can be manufactured repeatably. In addition, three separate processing steps are required, and the mesh and insulation materials are relatively expensive.

In the second common method of test strip construction, a die-cut spacer and hydrophilic lidding tape are used. This method typically involves laminating a die-cut spacer to a hydrophilic lidding tape. The lidding tape is in turn laminated to a base electrode on a substrate. In most cases, the adhesive used at all of the interfaces is pressure sensitive. The thickness of the spacer and layers of adhesive, coupled with the two-dimensional area removed from the spacer, define the volume of the sample cell.

A disadvantage of this second method is that gumming problems are often encountered when cutting pressure sensitive adhesives. Test strip manufacturing equipment is typically what gums up, but test strip ports on a user's meter can also be disabled by fouling caused by the adhesives. Additionally, mechanical punches can only be scaled down to a certain size. Also, in this process registration is critical in all planes, and the materials used are expensive.

Applying a reagent coating during the manufacture of test strips presents a challenge in situations where pad printing is not suitable. This challenge has been solved in two different ways, slot coating and spraying, each of which is described in turn below.

Slot coating uses a slot die and reagent pump to dose material onto a moving web. The pump rates, web transport rates, reagent rheology and slot geometry are all critical factors in achieving the desired coating. This method can be an ideal way of applying low viscosity reagents in a controlled manner at high speeds. However, it suffers from a number of problems. The first problem is that it is a continuous process and therefore coats areas of the web that are not functionally required for the assay. This not only is wasteful of reagent but also causes variations in height on the sides of the sample chamber, creating problems when sealing the chamber. If the sample chamber is not well sealed, the sample blood may leach away from the defined measurement area and provide erroneous results. Finally, providing a uniform stripe with the slot coating method can be problematic with some liquids since thicker bands of material are often found at the edges of the coated stripe.

Spraying is another method of laying fine coatings of reagent onto moving webs but also suffers from some disadvantages. In a reversal of the situation seen with slot coating, it is not uncommon for the center of the stripe to be thicker than the edges. This helps with sample chamber sealing, but is also not uniform. Since spraying is also a continuous process, it too is wasteful of reagent, and it is difficult to define areas accurately without masks.

Even with tight controls on strip manufacture, there typically is variation across different strip lots. In order to maintain accurate test results, some type of strip calibration is usually employed. For example, a representative sample of strips from each lot can be tested after manufacture. A calibration code can be determined from the testing and this code can be provided with each strip in the associated lot, such as on a packaging label. Before use of each package of test strips, the code can be entered into the meter, thereby calibrating the meter with the particular strips being used to provide accurate test results. However, this requires the user to perform an extra step. Furthermore, if the user neglects to enter a new calibration code for a new package of strips or enters the code incorrectly, inaccurate test results may be obtained, potentially causing harm to the user. Some manufacturers have resorted to providing a machine readable code on each strip or strip packaging that can be read directly by the meter during use. While this may reduce errors, these systems are not foolproof and add cost to the test strips and meters. Another method of reducing calibration issues is to supply a sub-set of test strip production, having a given calibration code, to a given customer base having meters that are already calibrated for use with those particular test strips. The remainder of the test strip production is labeled with calibration codes and supplied to a different customer base having meters requiring manual entry of calibration codes. This method is only effective for the portion of customers that do not need to use the calibration codes. Furthermore, product supply problems can develop if the calibration distribution does not match the demand of both meter bases.

SUMMARY OF THE INVENTION

According to aspects of some embodiments of the present invention, an in vitro analyte monitoring system may be constructed to operate with a minimum of analyte fluid. In one embodiment, a sensor may be formed by locating at least one electrode on a substrate, providing an embossed channel in the electrode, coating the channel with a reagent and covering the channel with a hydrophilic lidding tape. An opening to the channel may be provided at a distal end of the sensor so that when an analyte is applied to the opening, it is drawn into the channel by surface tension (i.e. wicking). A vent may be provided near an opposite end of the channel so that when the analyte fills the channel, air previously filling the channel can be evacuated through the vent. Aspects of the present invention are well suited for use with amperometric, coulometric, potentiometric and other sensor types.

According to other aspects of the invention, the embossing process may be performed either before or after the electrode(s) is applied to the substrate. In one embodiment, electrodes may be applied to a non-conducting substrate before a channel is embossed. For example, gold may be sputtering onto the substrate with a mask to form multiple electrodes separated by portions of the non-conducting substrate surface. Alternatively, an entire substrate surface may be sputtered with portions later being etched away to form spaces between multiple electrodes. In either case, a channel or channels may then be embossed into the electrode on the flat substrate. An advantage to this approach of post-embossing is that flat surfaced substrate material with electrodes formed thereon can be purchased from a large number of sources and then later embossed. With this approach it may also be easier to control the final dimensions of an embossed channel if the embossing step is one of the last steps to be performed before the sensor is assembled.

In another embodiment, a channel or channels may be embossed into a sensor substrate before an electrode or electrodes are formed on the substrate. With this pre-embossing approach, a much thinner coat of conductor can be used. This may be particularly advantageous when using expensive conductors such as gold. In addition, conductor materials that are more brittle can be considered for use with the pre-embossing approach.

According to other aspects of the invention, an embossing process used may be a rotary or a flat bed process. Various channel cross-sections may be employed, such as rectangular and V-shaped. According to one embodiment, embossed channels may have a semi-circular cross-section and may have a depth of less than about 200 microns. More preferably, the channels may be less than about 100 microns deep. Most preferably, channels may be less than about 50 microns deep. The active length of the test chamber channel may often be dictated by the layout of the test strip. According to one embodiment, an embossed channel is aligned with a longitudinal axis of a test strip. Other orientations may also be used. In one embodiment, the active length of an embossed channel (i.e. the length containing electrodes and reagent) may be less than about 10 mm. More preferably, the active length may be about 2 to 7 mm, and most preferably the length may be about 3 to 4 mm.

According to aspects of the present invention, the above geometries may provide sample chambers with highly repeatable volumes as well as electrode surface areas from strip to strip, thereby increasing accuracy. In a particular embodiment, sample chamber volumes may be less than about 200 nanoliters, more preferably may be less than about 50 nanoliters, and most preferably may be less than about 20 nanoliters.

According to aspects of the invention, reagent may be applied to the sample chamber channel through the use of a needle and squeegee, although other methods such as slot coating or spraying may also be used. Test strips are preferably manufactured in rows with the test strips attached side-by-side, and then singulated into individual test strips, such as by slitting or cutting, as one of the last manufacturing steps. In one embodiment, one or more rows may form a moving web during manufacture. Reagent may be pumped through a needle or needles onto the moving web and a squeegee used to spread the reagent and wipe the excess from the web. Alternatively, test strips may be formed in individual sheets before being singulated, and the needle(s) and squeegee(s) may be moved relative to the sheets to apply and spread the reagent.

Needle and squeegee deposition may take advantage of the volume of a channel already having been defined by an embossing step. The channel and surrounding area may have reagent deposited by the needle dosing system, which is then spread by the squeegee. The squeegee may collect and remove reagent from the flat areas surrounding the channel while leaving the channel fully filled. The wet reagent may then be dried to leave behind a thin film only in the channel. The final coat weight may typically be governed by reagent viscosity, squeegee hardness, squeegee pressure and reagent dilution. The delivery rate of the needle dosing system may be either perfectly balanced to the usage rate or may be in excess with a re-circulation or total loss system employed on the squeegee.

According to other aspects of the present invention, a process for trimming the ends of the test strips may be provided to calibrate the sensors. After patterning electrodes, embossing, reagent coating and hydrophilic lid lamination as described above, the sensors may essentially be functional. At this stage, preferably before individual sensors are separated from each other, a representative sample of sensors may be tested to ascertain at least one calibration parameter of the batch, such as a slope and/or intercept of a calibration curve. Through characterization at the design stage of the sensors, a range of slopes and/or other calibration parameters expected of the design may be found and a lower value may be selected for product release. By trimming the working area on the remaining electrodes the slope may then be adjusted to match this lower product release value. This trimming process can produce sensors that all have essentially the same calibration slope, thereby eliminating the need to mark the sensors with a calibration code and require that the code be entered into the test meter before use. The embossed test strip design embodiments described above are particularly well suited to such trimming due to their long channel lengths in relation to their cross sectional areas, and the fact that sensor registration need not be performed in more than one direction during the trimming process.

Various analytes may be monitored using aspects of the present invention. These analytes may include but are not limited to lactate, acetyl choline, amylase, bilirubin, cholesterol, chorionic gonadotropin, creatine kinase (e.g., CK-MB), creatine, DNA, fructosamine, glucose, glutamine, growth hormones, hematocrit, hemoglobin (e.g. HbA 1 c), hormones, ketones, lactate, oxygen, peroxide, prostate-specific antigen, prothrombin, RNA, thyroid stimulating hormone, and troponin, in samples of body fluid. Meters may also be configured to determine the concentration of drugs, such as, for example, antibiotics (e.g., gentamicin, vancomycin, and the like), digitoxin, digoxin, drugs of abuse, theophylline, warfarin and the like. Such analytes can be monitored in blood, interstitial fluid, saliva, urine and other bodily fluids.

BRIEF DESCRIPTION OF THE DRAWINGS

Each of the figures diagrammatically illustrates aspects of the invention. Of these.

Variation of the invention from that shown in the figures is contemplated.

DETAILED DESCRIPTION

The following description focuses on one variation of the present invention. The variation of the invention is to be taken as a non-limiting example. It is to be understood that the invention is not limited to particular variation(s) set forth and may, of course, vary. Changes may be made to the invention described and equivalents may be substituted (both presently known and future-developed) without departing from the true spirit and scope of the invention. In addition, modifications may be made to adapt a particular situation, material, composition of matter, process, process act(s) or step(s) to the objective(s), spirit or scope of the present invention.

Figure 1:
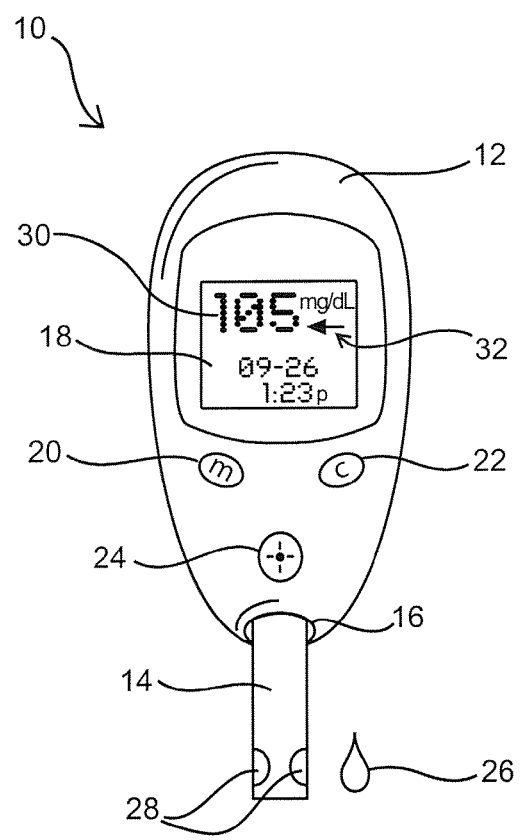
FIG. 1 is a plan view showing a test strip sensor in use with a glucometer.

FIG. 1 shows a top view of an exemplary analyte system 10, a glucometer system in this particular embodiment. System 10 includes a handheld meter 12 and disposable test strip sensor 14. Test strip 14 can be inserted into and removed from test strip port 16 of meter 12 for physical and electrical interconnection therewith. Meter 12 includes a liquid crystal display 18 for displaying information to the meter user, and buttons 20, 22 and 24 for receiving input from the user.

In general, to take a blood glucose measurement with meter 12, a user inserts a new test strip 14 into port 16 of meter 12. Either before or after strip insertion into the meter, a user lances a fingertip or other part of the body (i.e. an alternate site) to draw a small drop of blood 26 to the surface of the skin. The meter and strip are positioned over the drop of blood 26 so that one of the sample chamber ends 28 is touching the drop of blood 26. While this particular example teaches the use of a side-fill strip, it should be noted that an end-fill, top-fill or other type of test strip may be utilized, as will be later described. Moreover, the analyte testing need not use a test strip at all. For instance, a rotary test wheel having multiple sensors may be provided instead of individual test strips. In the present example, surface tension (wicking) automatically draws a small amount of blood 26 into the sample chamber and an electrochemical test is automatically performed by meter 12 to determine the glucose concentration in the blood 26. The glucose level 30 is then displayed on meter 12.

Figure 2:
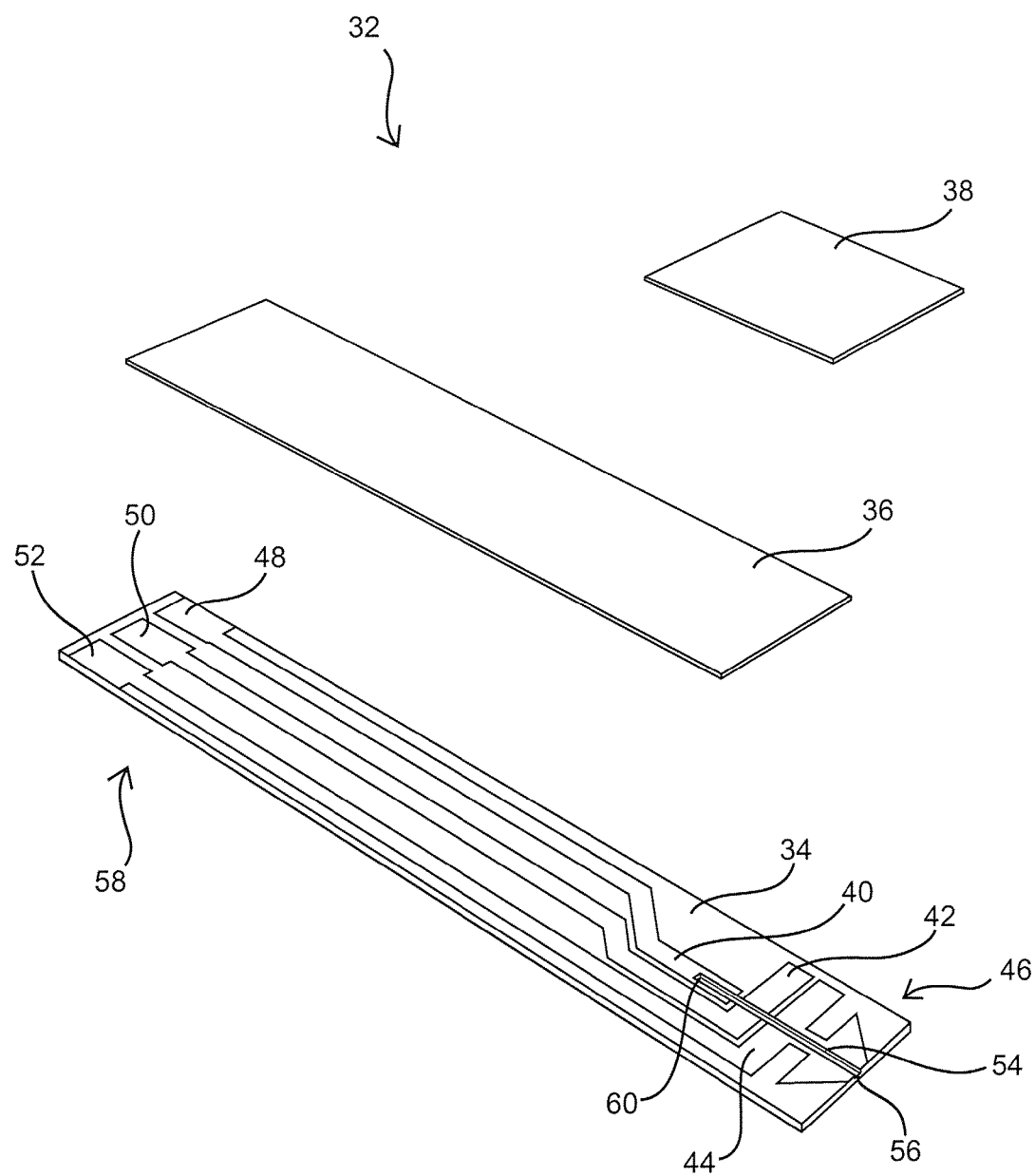
FIG. 2 is an exploded perspective view showing components of an exemplary embodiment of a test strip sensor constructed according to aspects of the present invention.
Figure 3:
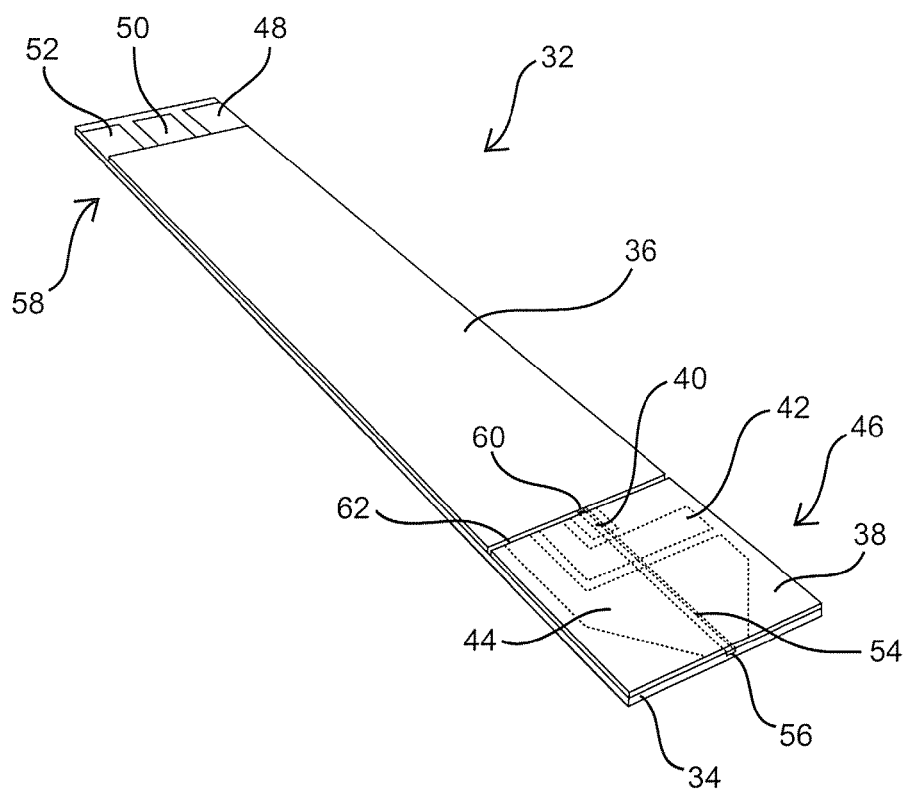
FIG. 3 is a perspective view showing the components of FIG. 2 in an assembled configuration.

Referring to FIGS. 2 and 3, an exploded view of an exemplary test strip sensor 32 constructed according to aspects of the present invention is shown. In this embodiment, sensor 32 includes a substrate 34, a cover strip 36 and lidding tape 38. A fill trigger electrode 40, a working electrode 42 and a reference electrode 44 can be patterned near a distal end 46 of substrate 34. Conductive electrodes 40, 42 and 44 may be separated by portions of non-conductive substrate 34, and may be linked by conductive traces to connector pads 48, 50 and 52, respectively. During use of test strip 32, connector pads 48, 50 and 52 each may electrically connect with associated connector contacts (not shown) within meter 12 shown in FIG. 1. Fewer, additional or different electrode types may be used. For example, fill electrode 40 may be omitted, and/or a second working electrode may be added to allow for hematocrit compensation.

In this embodiment, channel 54 is embossed into substrate 34 and traverses each of the electrodes 40, 42 and 44. A reagent is added to channel 54, an example of which is later described below. Lidding tape 38 may be applied to substrate 34, such as with a pressure sensitive adhesive to cover channel 54. Cover strip 36 may be added, such as with a pressure sensitive adhesive, mainly for aesthetic reasons and to protect the conductive traces. The above steps create a functional test strip, as shown in FIG. 3. Additional manufacturing steps may be performed, as will be later described.

The above construction forms a sample test chamber, bounded on the bottom by channel 54 in substrate 34, and on the top by lidding tape 38. An open end 56 of the sample chamber, located at or near the distal end 46 of test strip 32, allows sample fluid such as blood to enter the sample chamber. Lidding tape 38, its adhesive, and the materials forming substrate 34 and electrodes 40, 42 and 44 all are preferably hydrophilic. This arrangement allows the sample chamber to automatically fill with sample fluid by surface tension (wicking) when opening 56 is placed in contact with the fluid. Preferably, the dimensions and tolerances of channel 54 and lidding tape 38 are selected to ensure that channel 54 extends towards the proximal end 58 of strip 32 farther than lidding tape 38 to create a vent 60. Vent 60 allows air displaced by the filling fluid to easily escape the sample chamber without impeding fluid flow. A gap 62, as shown in FIG. 3, can be left between cover strip 36 and lidding tape 38 to help ensure that vent 60 is not blocked. In an alternative embodiment, cover strip 36 may be omitted altogether to reduce material and assembly costs and to keep vent 60 exposed. In another alternative embodiment, one of cover strip 36 and lidding tape 38 may overlap the other. For example, cover strip 36 may overlap lidding tape 38 by about 1 mm. Since the edge of the lower layer being overlapped has some thickness which creates a step, the upper layer is unable to form a perfect seal against the step. This incomplete seal extends the vent laterally along the step out to each side of test strip 32.

Figure 4:
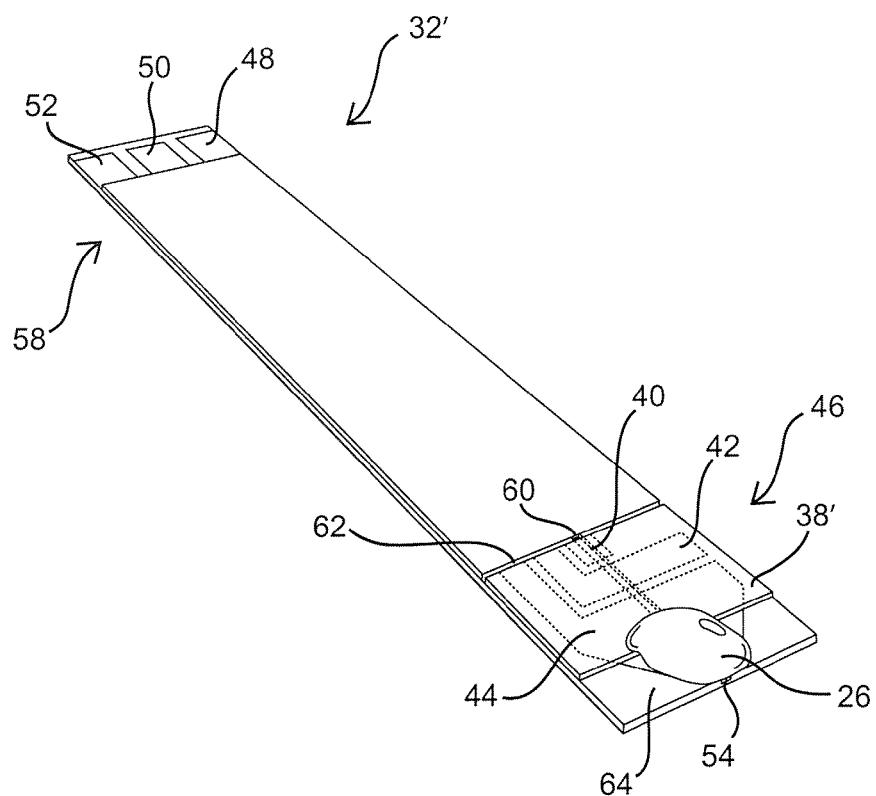
FIG. 4 is a perspective view showing an alternative embodiment sensor.

Embossed channel 54 may align with the longitudinal axis of strip 32 to create an end-fill strip, such as shown in FIG. 3. In an alternative embodiment, the channel may be perpendicular to the strip axis. An example of such a side-fill arrangement is shown in FIG. 1, with one sample chamber end 28 serving to fill the chamber with fluid in this embodiment, and the sample chamber end 28 on the opposite side of the strip 14 serving to evacuate escaping air. Other configurations for embossed channel 54 may also be used. FIG. 4 illustrates a variation of strip 32 shown in FIG. 3. In this alternative embodiment, the lidding tape 38' of strip 32' is shortened so that it does not extend to the end of strip 38'. In this embodiment, portions of channel 54 and substrate 34 are exposed to create a landing pad 64 for receiving blood or other analyte, thereby forming a top-fill strip. In use, a drop of blood 26 can be placed on landing pad 64 adjacent to or on top of the outer edge of lidding tape 38', as shown in FIG. 4. Blood 26 is wicked into channel 54 between lidding tape 38' and substrate 34 and is tested as previously described. Such an arrangement may be advantageous in settings such as hospitals where an analyte sample may be applied to the test strip by pipette.

According to aspects of the present invention, channel 54 may be embossed before or after electrodes 40, 42 and 44 are patterned on substrate 34. When channel 54 is embossed after electrodes are patterned on substrate 34, materials and processes may be chosen to avoid excessive damage to the electrodes, such as straining the electrode material(s) so much that their resistances increase drastically or the materials actually break. Such problems may be avoided by using a ductile electrode material like gold or similar metals, and/or by increasing the thickness of the electrode material(s). Male and female embossing tools may also be designed to reduce excessive material flow, thereby alleviating the above problems. A thicker and/or softer substrate and a shallower channel are other factors that can lessen the damage to the electrodes. By adjusting the tools, materials, thicknesses and processes used for making channel 54, an acceptable balance between channel depth and electrode damage can be struck for a particular set of sensor requirements.

A preferred substrate material may be PVC since it embosses readily. Another preferred material may be polyester. Polyester may not emboss as readily as PVC, but its use may facilitate faster reagent drying times. Polyester may be heated to 75 degrees Celsius without shrinkage, while PVC should not be heated above 55 degrees C. Polypropylene may be another preferred substrate material since it offers a compromise between the properties of PVC and Polyester.

With the tools, methods and materials described above, a test strip 32 having a very small sample volume and very repeatable geometric features may be produced. The small sample volume allows users to perform "alternate site testing" (i.e. at locations other than the fingertips) and allows less blood to be drawn. This in turn reduces or eliminates the pain involved with drawing blood, may reduces the mess of blood samples on the skin and causes less trauma to the body. According to aspects of the present invention, sample sizes may be less than about 20 nanoliters. Additionally, the repeatable geometric features that can be achieved by the test strips disclosed herein further increase the accuracy and precision of analyte testing with the strips.

Figure 5:
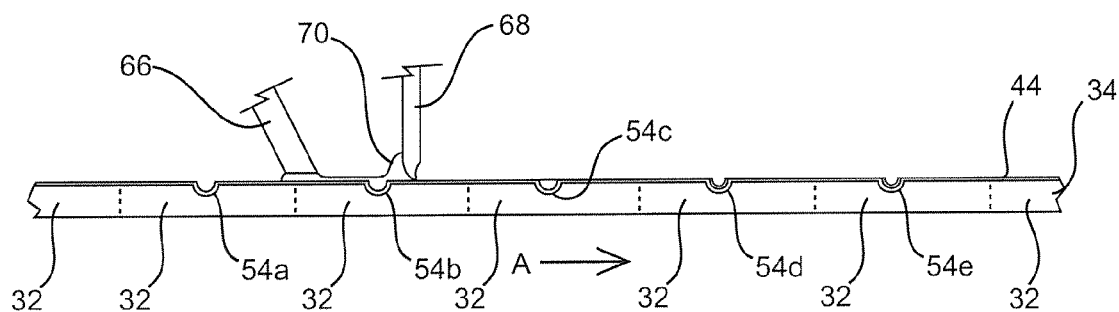
FIG. 5 is a side elevational view showing reagent being dispensed and distributed on a series of sensors according to aspects of the present invention.

Referring now to FIG. 5, an exemplary arrangement for applying reagent during the manufacture of test strips 32 is shown. In this embodiment shown, test strips 32 are formed side by side on a continuous web of substrate material 34, to be singulated into individual strips 32 during a later manufacturing process. Prior to the stage shown in FIG. 5, substrate 34 may be patterned with electrode material 44 and other electrodes (not shown), and channels 54a-54e may be embossed into the electrodes and/or substrate 34, as previously described above. The web of substrate material 34 may then be moved in the direction of Arrow A shown, under stationary reagent fill needle 66 and squeegee 68. Reagent 70 may be pumped, gravity fed or otherwise supplied through needle 66 onto moving substrate 34. Squeegee 68 can help spread reagent 40 across channels 54 and wipe excess reagent from the electrodes and substrate 34. Essentially all reagent 70 may be removed from the surface of substrate 34, leaving reagent 70 only in channels 54, which are then preferably full. Reagent 70 may be precisely metered onto substrate 34 to avoid wasting reagent 70. Alternatively, more reagent 70 than is needed may be supplied to substrate 34 to ensure complete coverage, and the excess may be recycled or discarded. FIG. 5 depicts a yet to be filled channel 54a, a channel 54b in the process of being filled with reagent 70 by needle 66 and leveled by squeegee 68, a channel 54c that has been filled and leveled, and two channels 54d and 54e that have been filled, leveled and now dried, leaving only a thin layer of reagent 70 along the channels.

Depending on the configuration of substrate web 34 and/or other parameters, single or multiple reagent needles 66 and/or single or multiple squeegees 68 may be utilized. Multiple needles may provide the same or different reagents to substrate 34. Needle(s) 66 need not have a circular or oval opening, but rather may have an elongated slot or a different shaped orifice. Squeegee(s) 68 need not be separate from needle(s) 66, but may be incorporated therein. The above arrangements may be utilized in batch processes rather than with the roll stock depicted. For example, substrate cards (not shown) containing a finite array of test strips 32 can be coated with reagent 70 and leveled by holding the cards stationary while moving needle(s) 66 and squeegee(s) 68 (either separately or in tandem) over the test strip cards.

Figure 6:
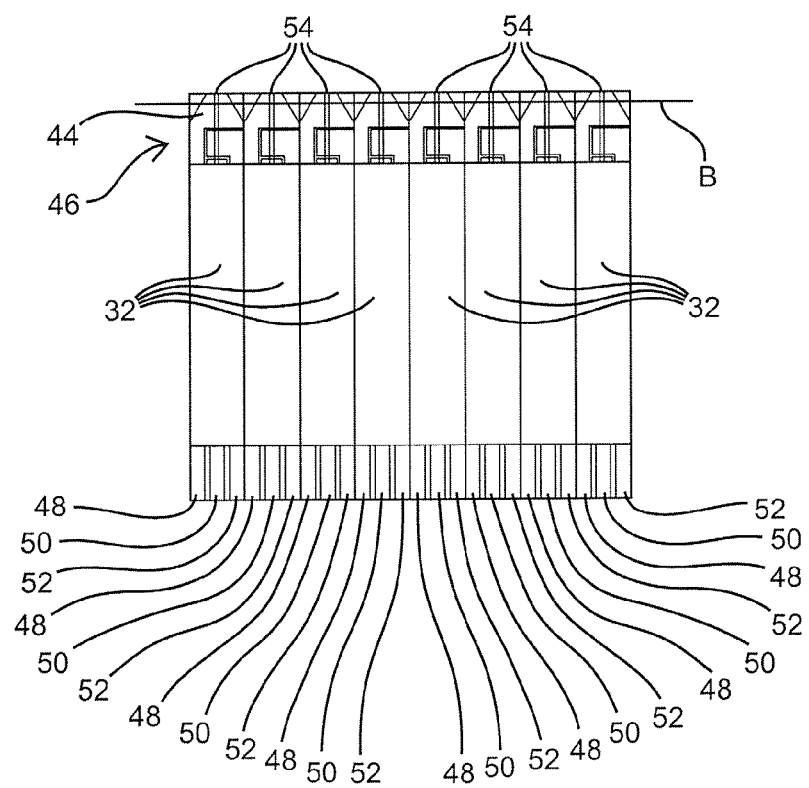
FIG. 6 is a plan view depicting a trimming process according to aspects of the present invention.

Referring now to FIG. 6, an exemplary embodiment is shown for trimming test strips 32 according to aspects of the present invention. After test strips 32 are functional, a representative sample may be tested. A sufficient number of test strips should be tested (or in other words a "batch size" should be small enough) so that it may be safely assumed that all test strips 32 in each particular batch if tested would yield substantially the same test results as the representative sample. Based on the test results, it may be determined that the entire batch has certain calibration characteristics, such as having a calibration curve with a particular slope. Rather than labeling the batch with the calibration characteristic (e.g. slope) and calibrating a meter 12 to the strip 32 during use, strip 32 may be modified during manufacture to "calibrate" it to the meter 12. By decreasing the volume of covered channel 54 and the area of the working electrode 44, the slope of a strip's calibration curve can be reduced to a preset value. To reduce the electrode area of an essentially finished test strip 32, a relatively small portion of the distal end 46 of the test strip 32 may be removed. This can be accomplished by trimming a series of unsingulated test strips 32 along line B, such as by slitting or cutting, as shown in FIG. 6. The location of cutting line B may be varied depending on how much functional change to strips 32 is desired. A representative sample of the trimmed test strips 32 may again be tested to ensure that each batch now has essentially the same characteristics. After trimming (if needed), test strips 32 may be separated from each other. Alternatively, test strips 32 may be singulated first and then trimmed, if needed. The above-described testing and trimming procedures may be conducted before or after any aging process. With use of the above manufacturing method, the need for user calibration can be eliminated. Also, the corners of the distal ends 46 of strips 32 may be chamfered to match the edges of working electrodes 44 shown in FIG. 6 to increase user comfort and ease of use.

As previously discussed above, a ductile electrode material may be chosen to avoid excessive damage to the electrode during an embossing step. The following discussion is intended to provide definition to the term "ductile". The material response for ductile and brittle materials are exhibited by both qualitative and quantitative differences in their respective stress-strain curves. Ductile materials withstand large strains before rupture; brittle materials fracture at much lower strains. The yielding region for ductile materials often takes up the majority of the stress-strain curve, whereas for brittle materials it is nearly nonexistent. Brittle materials often have relatively large Young's moduli and ultimate stresses in comparison to ductile materials.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with anyone or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

We claim:

1. A method of manufacturing a plurality of analyte sensor having similar operating characteristics, the method comprising:
    forming a plurality of substantially functional analyte sensors, each sensor having a channel extending to an edge of the sensor;
    testing at least one of the sensors to determine a calibration parameter of the sensor;
    based on the calibration parameter of the tested sensor, trimming a predetermined amount from one or more of the edges of the non-tested sensors, thereby reducing a sample volume of the channels of the sensors and changing a calibration parameter of the sensors.

2. The method of claim 1 further comprising the step of embossing the channels prior to forming the plurality of substantially functional sensors.

3. The method of claim 1, further comprising the step of packing the trimmed sensors in at least one package without an indication of a calibration parameter included with the package.

4. The method of claim 1, wherein the channels extend perpendicular to the longitudinal axis of the sensor.

5. The method of claim 4, wherein the channel is completely covered by a substrate.

6. The method of claim 1, wherein the trimming of the predetermined amount from the edges of the non-tested sensors decreases an electrode area in each of the non-tested sensors.

7. The method of claim 1, further comprising:
    separating the non-tested sensors into individual sensors.

8. The method of claim 7, wherein the separating of the non-tested sensors is after the trimming of the predetermined amount from the edges of the non-tested sensors.

9. The method of claim 1, further comprising:
    testing at least one of the non-tested sensors to determine a new calibration parameter of the non-tested sensors;
    based on the new calibration parameter, trimming a predetermined amount from the edges of the non-tested sensors that have previously been trimmed, thereby reducing a sample volume of-the channels of the non-tested sensors and again changing a calibration parameter of the non-tested sensors.

10. The method of claim 9, further comprising:
    separating the non-tested sensors into individual sensors before the testing to determine the new calibration parameter.

11. The method of claim 9, further comprising:
    separating the non-tested sensors into individual sensors after the testing to determine the new calibration parameter and after the trimming of the predetermined amount based on the new calibration parameter.

12. The method of claim 1, further comprising:
    chamfering corners of the edge of the non-tested sensors.

13. The method of claim 1, wherein the channels extend longitudinally along the sensors.

14. The method of claim 1, further comprising:
    forming the channels after patterning a plurality of electrodes on the sensors, wherein the forming of the plurality of substantially functional analyte sensors comprises patterning the plurality of electrodes on the sensors, and wherein each channel traverses at least one electrode.

15. The method of claim 14, wherein the forming of the plurality of substantially functional analyte sensors comprises:
    providing a substrate having the channels embossed in a surface of the substrate, wherein the channels extend perpendicular to the longitudinal axis of the sensor along the surface of the substrate, and wherein openings for the channels extend perpendicular to the longitudinal axis of the sensor along the surface of the substrate;
    locating at least one needle adjacent to the surface of the substrate and dispensing a reagent from the needle onto the surface;
    contacting the surface with at least one squeegee; and
    causing relative movement between the substrate and the needle and between the substrate and the squeegee,
    wherein the needle and the squeegee cooperate to substantially fill the channels with reagent via the openings and leave a remainder portion of the surface generally free of reagent.

* * * * *